United States Patent
Hongou et al.

(10) Patent No.: US 8,834,375 B2
(45) Date of Patent: Sep. 16, 2014

(54) ULTRASOUND PROBE AND ULTRASOUND DIAGNOSIS APPARATUS

(75) Inventors: Hironobu Hongou, Otawara (JP); Yasuo Miyajima, Utsunomiya (JP); Toru Hirano, Otawara (JP); Isao Uchiumi, Nasushiobara (JP); Nobuyuki Iwama, Nasushiobara (JP); Masaaki Ishitsuka, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/579,665

(22) PCT Filed: Dec. 20, 2011

(86) PCT No.: PCT/JP2011/079444
§ 371 (c)(1),
(2), (4) Date: Aug. 17, 2012

(87) PCT Pub. No.: WO2012/101937
PCT Pub. Date: Aug. 2, 2012

(65) Prior Publication Data
US 2012/0310096 A1    Dec. 6, 2012

(30) Foreign Application Priority Data
Jan. 27, 2011    (JP) ................. 2011-014930

(51) Int. Cl.
A61B 8/14    (2006.01)
A61B 8/00    (2006.01)
A61B 8/08    (2006.01)

(52) U.S. Cl.
CPC .................. *A61B 8/4483* (2013.01); *A61B 8/54* (2013.01); *A61B 8/5207* (2013.01); *A61B 8/56* (2013.01)
USPC ............................ 600/447; 600/437; 600/443

(58) Field of Classification Search
None
See application file for complete search history.

(56) References Cited

U.S. PATENT DOCUMENTS 6,126,602 A    10/2000    Savord et al.
(Continued)

FOREIGN PATENT DOCUMENTS

JP    5 7586    1/1993
(Continued)

OTHER PUBLICATIONS

International Search Report Issued Feb. 21, 2012 in PCT/JP11/79444 Filed Dec. 20, 2011.

*Primary Examiner* — Tse Chen
*Assistant Examiner* — Mark Remaly
(74) *Attorney, Agent, or Firm* — Oblon, Spivak, McClelland, Maier & Neustadt L.L.P.

(57) ABSTRACT

To be able to control an aperture in ultrasound transducer units comprised such that the signals from a plurality of ultrasound transducers are added and output. An ultrasound probe comprising a plurality of ultrasound transducers, a plurality of delay circuits, and an adder circuit, and configured to be able to control a reception aperture of ultrasound waves. The delay circuit performs a delay processing to reception signals. The adder circuit adds and outputs the reception signals for each predetermined group. The ultrasound probe further comprises a gate means. The gate means switches connection and disconnection of the signal path for each signal path arranged between the ultrasound transducer and the adder circuit. The gate means also connects only the signal path from the ultrasound transducer corresponding to the initial reception aperture that is previously set after the transmission of ultrasound waves within the cycle of the ultrasound waves and sequentially connects the corresponding signal path from the ultrasound transducer that is closer to the initial reception aperture according to the lapse in time of the reception period.

6 Claims, 9 Drawing Sheets

(56) References Cited

U.S. PATENT DOCUMENTS

2007/0145860 A1 6/2007 Aoki et al.
2008/0009727 A1* 1/2008 Kataguchi .................... 600/437
2010/0010350 A1* 1/2010 Baba et al. .................... 600/443

FOREIGN PATENT DOCUMENTS

| JP | 2007 167445 | 7/2007 |
| JP | 2007 185529 | 7/2007 |

* cited by examiner

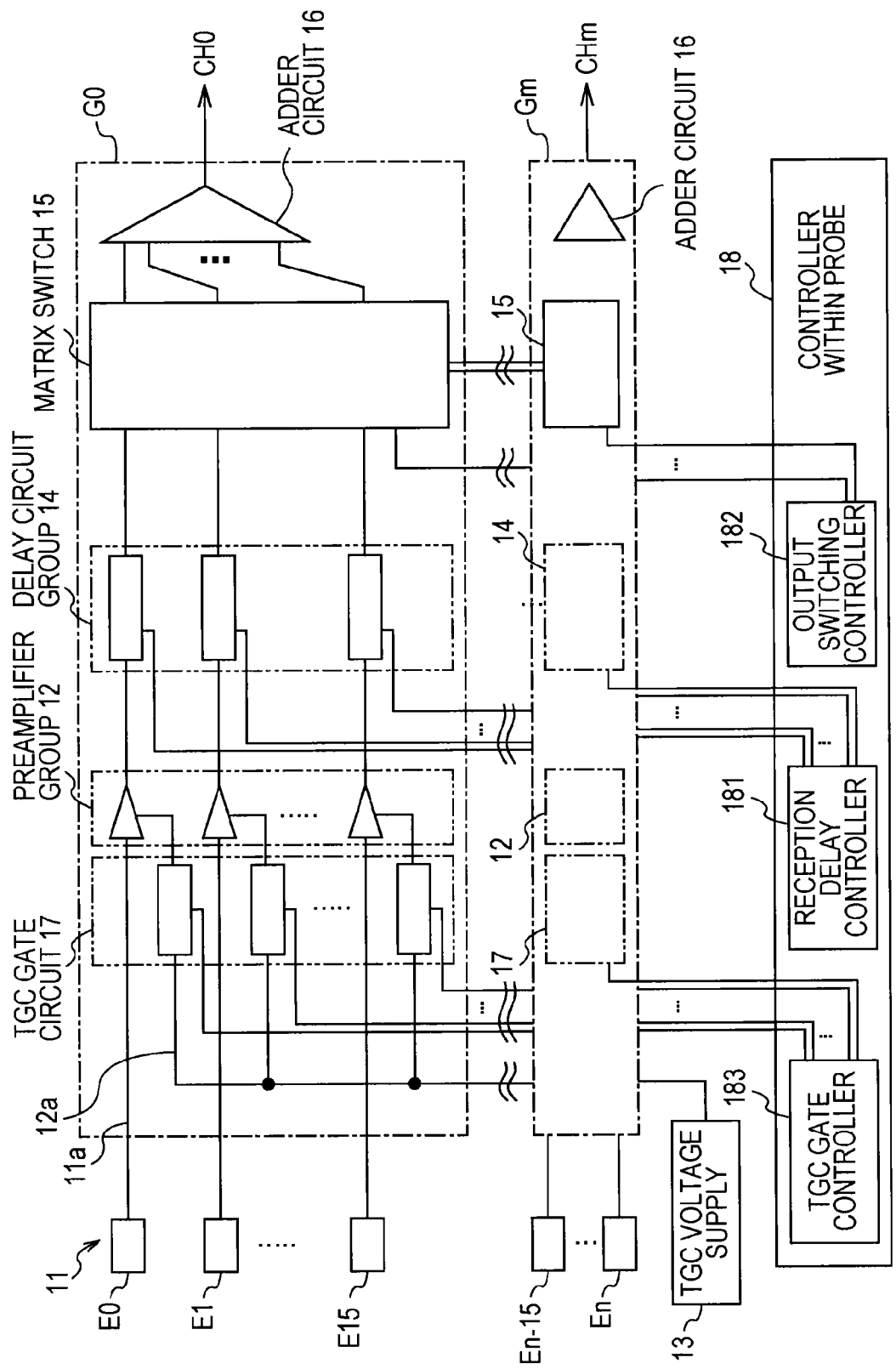

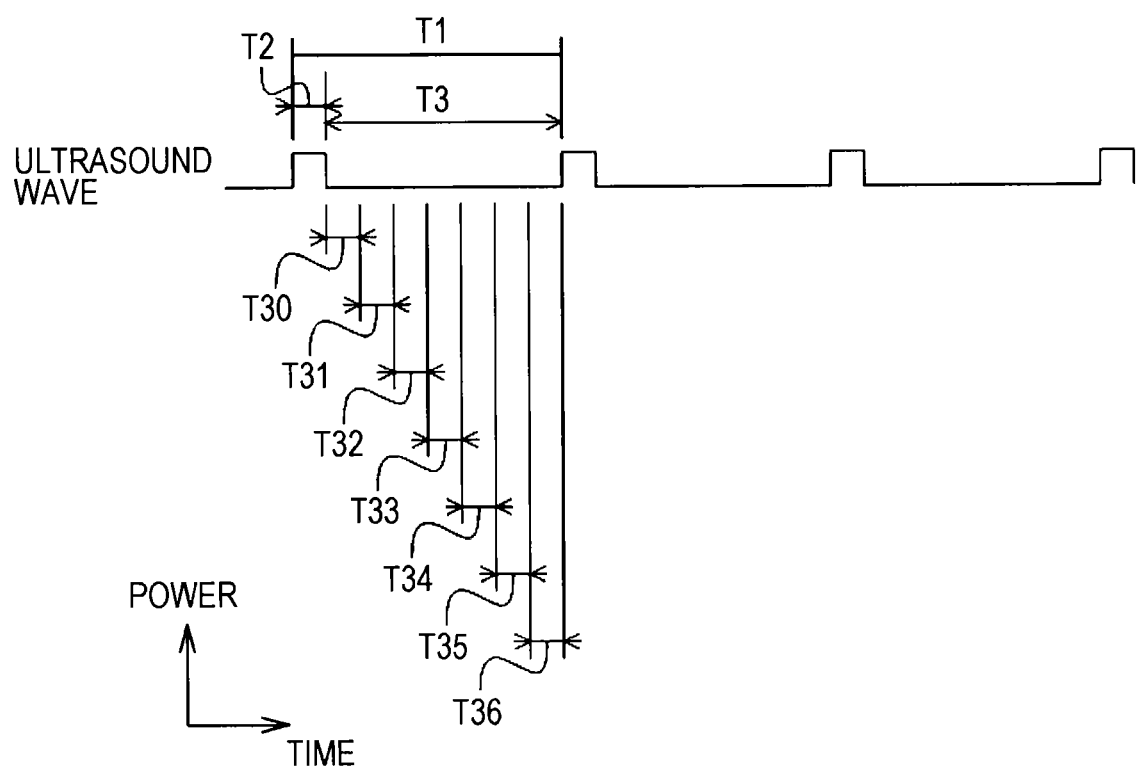

FIG. 4A
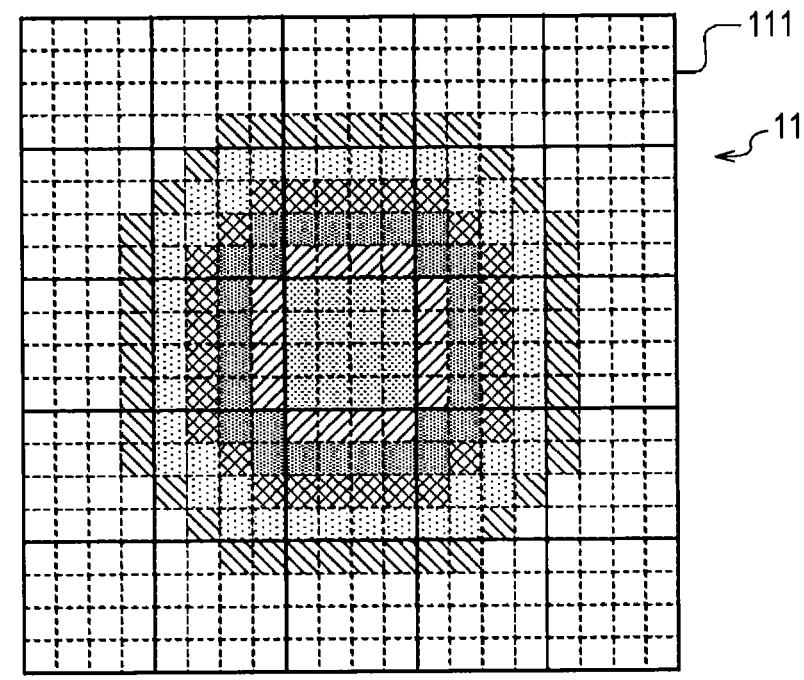
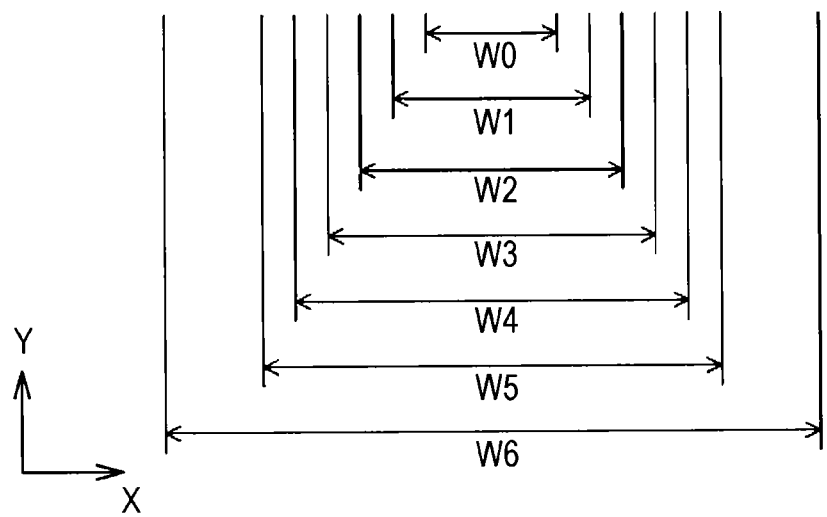
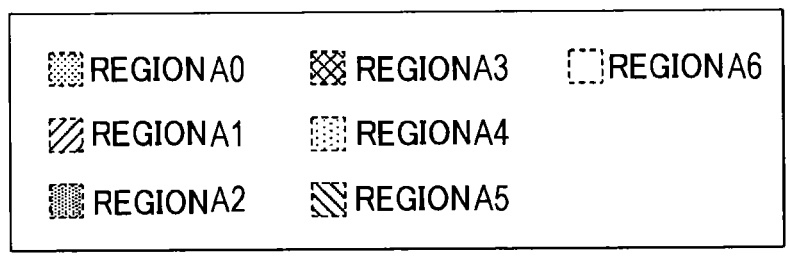

ULTRASOUND PROBE AND ULTRASOUND DIAGNOSIS APPARATUS

FIELD OF THE INVENTION

The embodiments of the present invention relate to an ultrasound probe and the technology of an ultrasound diagnosis apparatus.

BACKGROUND OF THE INVENTION

In an ultrasound two-dimensional (2D) array probe, etc., a few hundred to a few thousand ultrasound transducers are used. In this case, because when the probes are connected directly to an ultrasound diagnosis apparatus, a significant number of signal lines are required and the entire cable is thickened, resulting in some troubles in the operation. Therefore, in such an ultrasound probe, a sub-array reception delay circuit with a plurality of transducers as one group (sub-array) is used. Accordingly, since it is allowed to partially apply a reception delay processing in the ultrasound probe and add for each sub-array, it is possible to reduce the number of signal lines.

On the other hand, there is a technology known as an Aperture growth that improves the reception sound field at a short distance. In the case of reception signals from a portion which is close to a body surface, there is a large difference in the delay between an ultrasound transducer that is close to the center of the aperture and an ultrasound transducer that is away from the center of the aperture. Therefore, because the delay circuit cannot allow any difference in delay, reception quality may be deteriorated. In the Aperture growth, the aperture of an ultrasound probe is reduced when reflected waves from a portion which is close to a body surface are received, and the aperture is widened as the depth is increased. Accordingly, because the ultrasound transducer that is away from the center of the aperture is not used when reflected waves from a portion which is close to the body surface are received, the delay processing based on a large delay does not need to be performed, it is possible to improve the reception sound field at short distances.

Aperture control in the ultrasound diagnosis apparatus, including the Aperture growth, is performed by a reception circuit in a main body of the ultrasound diagnosis apparatus. However, in such a constitution, if comprised such that the signals from a plurality of ultrasound transducers as a 2D array probe are added and output for each sub-array, aperture control is performed in the sub-array units. Therefore, because the Aperture growth is also performed in the sub-array units, there is a problem in that image quality is more deteriorated compared to that of an Aperture growth in the transducer units. In addition, with type of scanning to move the center of an aperture, because the position of the center of the aperture is limited in the section that is packaged as a sub-array, it was difficult to perform fine scanning. Such problems are eliminated by providing signal lines for carrying out aperture control for each ultrasound transducer and carrying out aperture control in ultrasound transducer units. However, in the case of a large number of ultrasound transducers as a 2D array probe, because there is a problem in that the number of signal lines increases and the entire cable becomes thick as described above, it is difficult to employ such a method.

PRIOR ART DOCUMENTS

Patent Documents

[Patent Document 1] Japanese Published Unexamined Application No. 2007-167445

SUMMARY OF THE INVENTION

Problems to be Solved by the Invention

The embodiments of the present invention have been created in order to solve the abovementioned problems, with the object of being able to control an aperture in ultrasound transducer units comprised such that the signals from a plurality of ultrasound transducers are added and output.

Means of Solving the Problems

To achieve the abovementioned objects, the first aspect of this embodiment is an ultrasound probe comprising a plurality of ultrasound transducers, a plurality of delay circuits, and an adder circuit, and is configured to be able to control a reception aperture of ultrasound waves. The ultrasound transducer transmits ultrasound waves at a predetermined cycle and receives ultrasonic echoes from the inside of a subject. The delay circuit receives reception signals from each of the ultrasound transducers and performs a delay processing to each of the reception signals. The adder circuit adds and outputs the reception signals to which the delay processing is performed for each predetermined group. The ultrasound probe further comprises a gate means. The gate means is configured to be able to switch connection and disconnection of the signal paths for each signal path arranged between the ultrasound transducer and the adder circuit. The gate means also connects only the signal path from the ultrasound transducer corresponding to the initial reception aperture that is previously set after transmitting the ultrasound waves within the cycle of the ultrasound waves and sequentially connects a corresponding signal path from an ultrasound transducer that is closer to an initial reception aperture according to the lapse in time of the reception period. In addition, the second aspect of this embodiment is an ultrasound diagnosis apparatus comprising a plurality of ultrasound transducers, a plurality of delay circuits, and an adder circuit, and further comprises an ultrasound probe that is configured to be able to control a reception aperture of the ultrasound waves. The ultrasound transducer transmits ultrasound waves at a predetermined cycle and receives ultrasonic echoes from the inside of a subject. The delay circuit receives reception signals from each of the ultrasound transducers and performs a delay processing to each of the reception signals. The adder circuit adds and outputs the reception signals to which the delay processing is performed for each predetermined group. The ultrasound diagnosis apparatus receives the reception signals that are output from the ultrasound probe and performs phasing and addition on the reception signals to generate an ultrasound image. The ultrasound probe further comprises a gate means. The gate means is configured to be able to switch connection and disconnection of the signal paths for each signal path arranged between the ultrasound transducer and the adder circuit. The gate means also connects only the signal path from the ultrasound transducer corresponding to the initial reception aperture that is previously set after transmitting the ultrasound waves within the cycle of the ultrasound waves and sequentially connects a corresponding signal path from an ultrasound transducer that is closer to an initial reception aperture according to the lapse in time of the reception period.

In addition, the third aspect of this embodiment is an ultrasound probe comprising a plurality of ultrasound transducers, a plurality of delay circuits, an adder circuit, and a gate means. The ultrasound transducer transmits ultrasound waves and receives ultrasound echoes from the inside of a subject. The delay circuit receives reception signals from each of the ultrasound transducers and performs a delay processing to each of the reception signals. The adder circuit adds and outputs the reception signals to which the delay processing is performed for each predetermined group. The gate means is configured to be able to switch connection and disconnection of the signal paths for each signal path arranged between the ultrasound transducer and the adder circuit.

BRIEF DESCRIPTION OF THE DRAWINGS

FIG. 2 is a block diagram of the reception part of the ultrasound probe according to the first embodiment.

FIG. 3A is a diagram describing the relationship between the transmission timing and reception timing of ultrasound waves.

FIG. 4A is a diagram describing the control of an Aperture growth in the present embodiment.

DETAILED DESCRIPTION OF THE INVENTION

First Embodiment

Figure 1:
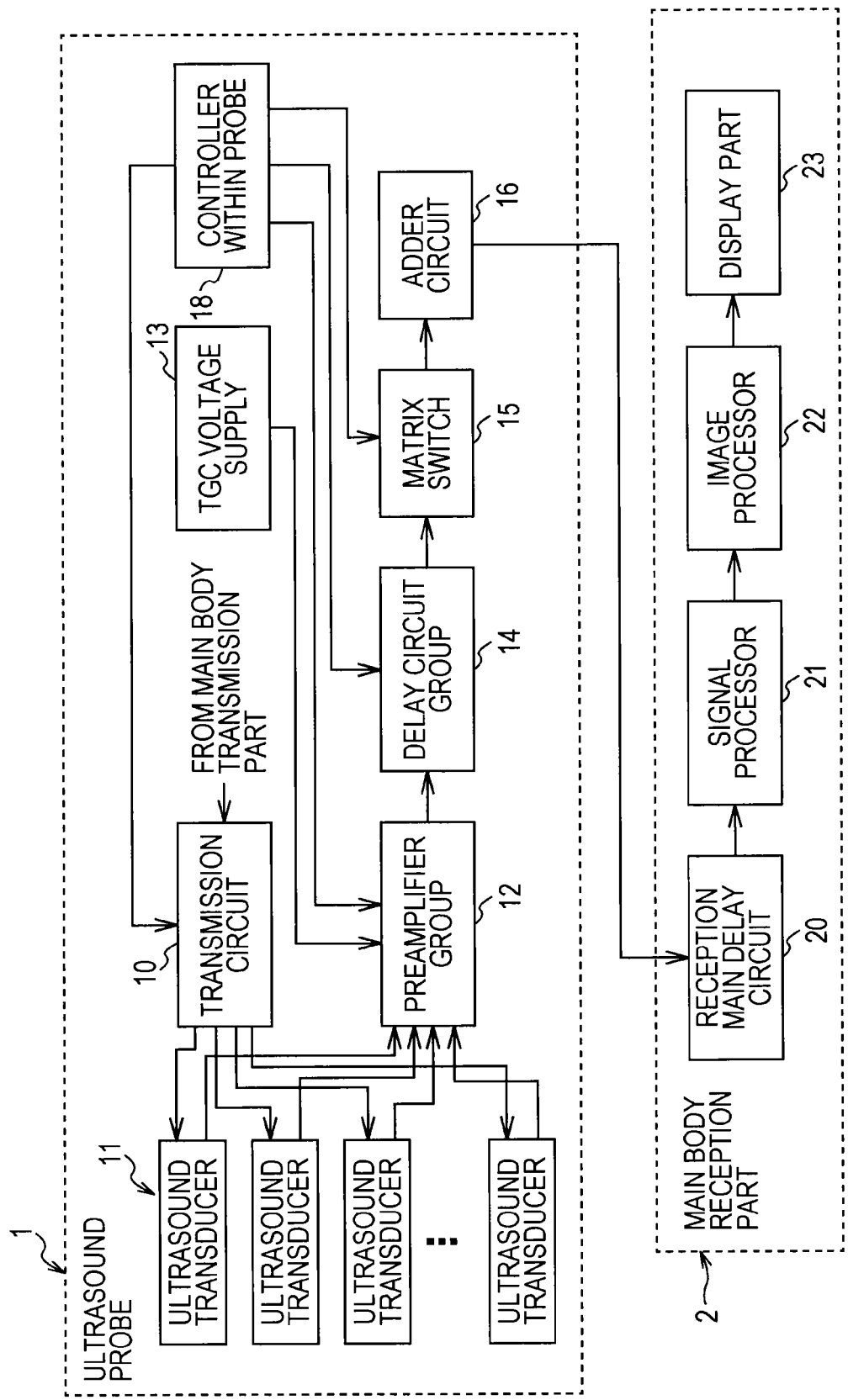
FIG. 1 is a block diagram of the reception part of the ultrasound diagnosis apparatus according to the present embodiment.

The ultrasound diagnosis apparatus according to the first embodiment perform to partial phase and add within the ultrasound probe on signals (hereinafter, referred to as "reception signals") that are received by a plurality of ultrasound transducers. Assuming such a constitution, the ultrasound diagnosis apparatus according to this embodiment controls an aperture that receives ultrasound waves for each ultrasound transducer. Wherein, in the following, the description of "aperture control" shall include both control of the position of an aperture (position of the center of an aperture) and control of the area (size) of an aperture. In the following, the constitution of the ultrasound diagnosis apparatus according to the present embodiment is described focusing on the constitution to receive ultrasound waves with reference to FIG. 1 and FIG. 2. Referring now to FIG. 1, the reception part of the ultrasound diagnosis apparatus according to this embodiment is configured to include an ultrasound probe 1 and a main body reception part 2.

The ultrasound probe 1 comprises a transmission circuit 10, an ultrasound transducer group 11, a preamplifier group 12, a TGC voltage supply 13, a delay circuit group 14, a matrix switch 15, an adder circuit 16, and a controller within probe 18.

Although not shown, the transmission circuit 10 comprises a clock generator, a divider cycle, a transmission delay circuit, and a pulser. The clock pulse generated by the clock generator is reduced, for example, to a rate pulse of approximately 5 KHz by the divider. This rate pulse is provided to the pulser through the transmission delay circuit to generate a high-frequency voltage pulse, and the ultrasound transducer group 11 is driven (mechanically oscillated) by this voltage pulse. Accordingly, ultrasound beams are irradiated from the ultrasound transducer group 11 towards an observation object in accordance with electrical signals transmitted from the transmission circuit 10.

The ultrasound transducer group 11 transmits and receives ultrasound waves with respect to an observation object (e.g., a heart). The ultrasound beams transmitted from each ultrasound transducer (hereinafter, referred to as "each transducer") comprising the ultrasound transducer group 11 are reflected on an interface with a different acoustic impedance, such as the boundary of a structure in the observation object, in response to the structure, motion, etc., in the observation object. Each transducer receives ultrasound waves reflected from the inside of the observation object. Each transducer converts the received ultrasound waves into electrical signals, and outputs them to the preamplifier group 12 via a signal line 11$a$ connected for each transducer. Wherein, the signal line 11$a$ is formed from the transducer to the adder circuit 16 for each transducer. This signal line 11$a$ is equivalent to a "signal path."

Referring now to FIG. 2, the controller within the probe 18 is a controller that controls the operation of each part within the ultrasound probe 1. The controller within the probe 18 includes a reception delay controller 181, an output switching controller 182, and a TGC gate controller 183. Wherein, the operation of the reception delay controller 181, the output switching controller 182, and the TGC gate controller 183 is described in the following, respectively.

The preamplifier group 12 comprises a plurality of preamplifiers. Each preamplifier receives reception signals that are received in a transducer via the signal line 11$a$ connected to the transducer comprising the ultrasound transducer group 11. The preamplifier performs processes such as low noise amplification or buffering in order to successfully transfer the ultrasonic echo signals that are received from a transducer.

The preamplifier according to the present embodiment is configured so as to be able to control a gain. A TGC (Time Gain Control) voltage supply 13 supplies TGC voltage for controlling the gain to each preamplifier via the signal line 12$a$. In other words, the gain of each preamplifier is determined by the TGC voltage supplied from the TGC voltage supply 13. The TGC voltage supply 13 changes the TGC voltage depending on the timing of receiving ultrasound waves. Accordingly, attenuated ultrasound waves are allowed to be kept at a constant level by controlling the gain greater when the ultrasound waves are reflected at a deeper position of the inside of a subject, for example. Each preamplifier outputs amplified reception signals to the delay circuit group 14.

A TGC gate circuit 17 is provided in the signal line 12$a$ connecting the TGC voltage supply 13 with a preamplifier. The TGC gate circuit 17 disconnects the supply of TGC voltage via the signal line 12$a$ temporarily, in response to instructions from the TGC gate controller 183. The TGC gate controller 183 is described below.

The gain of each preamplifier is set to zero or an extremely low value by disconnecting the supply of the TGC voltage from the TGC voltage supply 13. Accordingly, the preamplifier is allowed to disconnect signals that are output from a transducer via the signal line 11a (or allow the power to be reduced to a negligible level). In other words, each preamplifier switches connection and disconnection of the signal line 11a by controlling the presence or absence of the supply of the TGC voltage. Wherein, the preamplifier according to the present embodiment is configured to be able to switch connection and disconnection of the signal line 11a by controlling the presence or absence of the supply of the TGC voltage, which is equivalent to a "gate means."

The TGC gate controller 183 controls the operation of the TGC gate circuit 17. The TGC gate controller 183 is configured to be able to individually control the operation of each TGC gate circuit 17. Accordingly, the supply state of the TGC voltage is switched between supply and disconnection for each preamplifier. The gain of the preamplifier for which the supply of the TGC voltage is disconnected is zero or an extremely low value, and reception signals from a corresponding preamplifier are disconnected or become signals with extremely small power. With such a constitution, the control of an aperture such as an Aperture growth is performed in the transducer units by switching connection and disconnection for each signal line 11a. Wherein, detailed information regarding control of the Aperture growth is described below.

The delay circuit group 14 comprises a plurality of delay circuits. Each delay circuit receives reception signals output from a preamplifier; in other words, it receives reception signals output from a transducer and amplified in a preamplifier. Each delay circuit outputs by performing a delay processing to an output from a preamplifier. Delay data with which each delay circuit performs the delay processing to reception signals is calculated by the reception delay controller 181 and output to each delay circuit. The reception delay controller 181 is described later. Each delay circuit outputs reception signals to which the delay processing is performed for the matrix switch 15.

The reception delay controller 181 calculates the necessary delay based on the distance between a transducer and a focus point of the inside of a subject for each transducer comprising the ultrasound transducer group 11. The reception delay controller 181 controls the operation of the delay circuit by outputting the calculated delay as delay data to the delay circuit connected to the transducer corresponding to the delay. Accordingly, each delay circuit performs the delay processing for reception signals.

The matrix switch 15 mediates between the delay circuit group 14 and the adder circuit 16 that is provided for each sub-array. The matrix switch 15 outputs the signals input from each delay circuit comprising the delay circuit group 14 to the adder circuit 16. During this process, the matrix switch 15 switches the adder circuit 16 that will be a destination of these signals, for each signal that is input from a delay circuit. In this case, for example, it is preferable that the matrix switch 15 be provided for each sub-array and be configured to be able to transfer signals between the plurality of matrix switches 15. Accordingly, a signal input to a certain matrix switch is allowed to be output to the adder circuit 16 provided on the output side of another matrix switch, and it is possible to change the combination of transducers that constitute a sub-array.

The output switching controller 182 controls the destinations of reception signals by the matrix switch 15 based on the correspondence of each transducer and sub-array. Accordingly, the reception signals from transducers which are output from the delay circuit group 14 are output to the adder circuit 16 corresponding to the sub-array in which its transducer is included. Specifically, the output switching controller 182 controls the matrix switch 15 such that reception signals from transducers E0 to E15 are output to the adder circuit 16 corresponding to a sub-array G0, as shown in FIG. 2, for example. Similarly, the output switching controller 182 controls the matrix switch 15 such that reception signals from transducers En-15 to En are output to the adder circuit 16 corresponding to a sub-array Gm.

Wherein, if the combinations of the transducers comprising a sub-array do not need to be changed, the matrix switch 15 may not be provided. In this case, the reception signals that are output from the delay circuit group 14 are input to the adder circuit 16.

The adder circuit 16 is provided for each sub-array. The adder circuit 16 receives reception signals to which a delay processing is performed by the delay circuit group 14, via the matrix switch 15, and adds these reception signals. The adder circuit 16 outputs the added reception signals to the main body reception part 2. As shown in FIG. 2, the adder circuit 16 adds reception signals from these transducers, wherein, for example, the transducers E0 to E15 act as one sub-array G0, and outputs them to a channel CH0 in the main body reception part 2. Similarly, the adder circuit 16 adds reception signals from these transducers, wherein the transducers En-15 to En act as one sub-array Gm, and outputs them to a channel CHm in the main body reception part 2. Accordingly, the number of output signal lines from the ultrasound probe 1 can be reduced. In other words, the number of signal lines in a probe cable is reduced.

Referring now to FIG. 1, the main body reception part 2 comprises a reception main delay circuit 20, a signal processor 21, an image processor 22, and a display part 23.

The reception main delay circuit 20 comprises, for example, delay adder circuits such as digital beam former units, receives signals from the ultrasound probe 1, and performs to phase and add the signals. During this process, it may be a constitution in which an amplifier circuit such as a preamplifier is provided on the input side of the delay adder circuit to amplify signals by this amplifier circuit and perform to phase and add.

The signals on which phasing and addition are performed by the reception main delay circuit 20 are detected by the signal processor 21 and envelopes are extracted therefrom. Furthermore, the extracted envelopes are provided with coordinate transformation so as to coordinate with a cross-section of an observation object by the image processor 22 and with a gradation processing that is suitable for image display, and then displayed on the display part 23 as an ultrasound image.

Figure 3B:
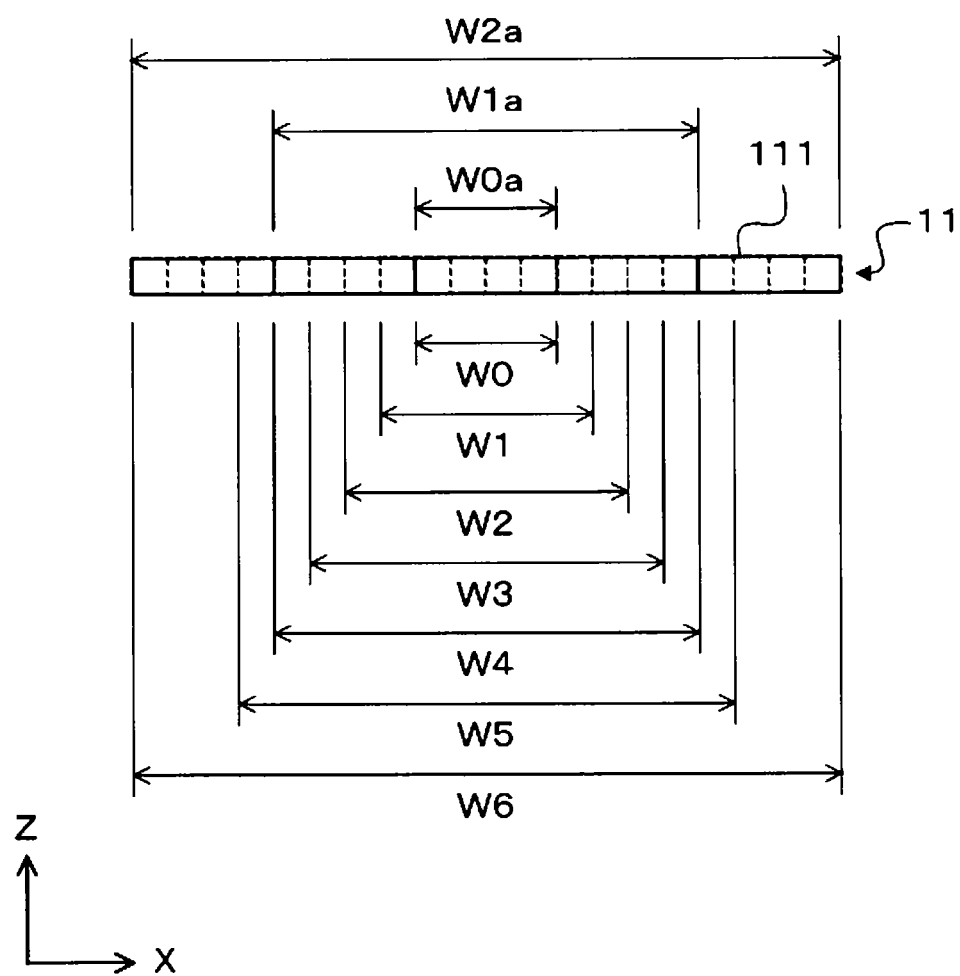
FIG. 3B is a diagram describing the operation of an Aperture growth.

Next, the control of the Aperture growth in the present embodiment is described with reference to FIG. 3A, FIG. 3B, FIG. 4A, and FIG. 4B. First, an overview of the Aperture growth is described with reference to FIG. 3A and FIG. 3B. FIG. 3A is a diagram describing the relationship between the transmission timing and reception timing of ultrasound waves. The vertical axis in FIG. 3A shows the power of ultrasound waves, while the horizontal axis shows time. FIG. 3B is a diagram viewing the ultrasound transducer group 11 from the side of a probe, and is a diagram for describing an operation of an Aperture growth based on the timing according to the transmission and reception of ultrasound waves shown in FIG. 3A. The Z-axis in FIG. 3B shows the direction of a lens that converges ultrasound waves, while the X-axis shows one array direction (a horizontal axis direction) of two-dimensionally arranged ultrasound transducers.

The ultrasound diagnosis apparatus according to the present embodiment uses pulse waves such as B-mode and drives each ultrasound transducer by dividing into a period during which ultrasound waves are transmitted and a period during which ultrasound waves are received, for example. T1 in FIG. 3A shows a transmission cycle for transmitting pulse waves. The transmission cycle T1 includes a period T2 during which ultrasound waves are transmitted and a period T3 during which ultrasound waves that are reflected from the inside of a subject are received. During the period T3, the ultrasound waves that are reflected at different depths inside a subject are received during different periods T30 to T36, respectively. This is because the time from when the transmitted ultrasound waves are reflected from the inside of a subject to when they reach an ultrasound transducer again gets longer as the depth at which the ultrasound waves reflect is deepened. For example, it is assumed that the depth is deepened in the order of a depth 1, a depth 2, . . . , and a depth 6 from the vicinity of a body surface. In this case, during the period T30 that is just after the period T2 during which ultrasound waves are transmitted, the ultrasound waves that are reflected in the vicinity of a body surface are received. In addition, the ultrasound waves that are reflected at the depth 1 are received during the period T31. In this way, during the period T2, ultrasound waves are received during an earlier period in order from a shallower depth to a deeper depth. In other words, ultrasound waves that are reflected at the depth 2, the depth 3, . . . , and the depth 6 are received during the period T32, T33, . . . , and T36, respectively. Wherein, the period T2 is equivalent to a "reception period" and the period T30 is equivalent to an "initial reception period".

In the case of controlling the Aperture growth, a reception aperture of ultrasound waves is gradually widened in the order of period T30, T31, . . . , T36 in FIG. 3A. This operation is described specifically with reference to FIG. 3A and FIG. 3B. W0 to W6 in FIG. 3B show the width of a reception aperture of ultrasound waves. For example, in the periods T30, T31, . . . , and T36 in FIG. 3A, as shown in FIG. 3B, a range of transducers that receive ultrasound waves and output reception signals is gradually increased to W0, W1, . . . , W6. Accordingly, the reception aperture gradually widens to W0, W1, . . . , and W6. By controlling in this way, when the ultrasound waves reflected in the vicinity of a body surface (corresponding to the period T30), the width of the reception aperture is narrowed to W0. The width W0 during the period T30 is equivalent to an "initial reception aperture." Wherein, W0a to W2a in FIG. 3B show the width of a reception aperture that is able to be set in a conventional ultrasound diagnosis apparatus. Because in a conventional ultrasound diagnosis apparatus the reception aperture was controlled for each sub-array 111, the width of the reception aperture had to be widened in the sub-array units as W0a, W1a, W2a. In contrast, the ultrasound diagnosis according to the present embodiment controls the reception aperture in the transducer units as W0 to W6 in FIG. 3B. Wherein, in the following, the description of "widen the reception aperture" means that the number of transducers for receiving ultrasound waves and outputting reception signals is increased.

Figure 4B:
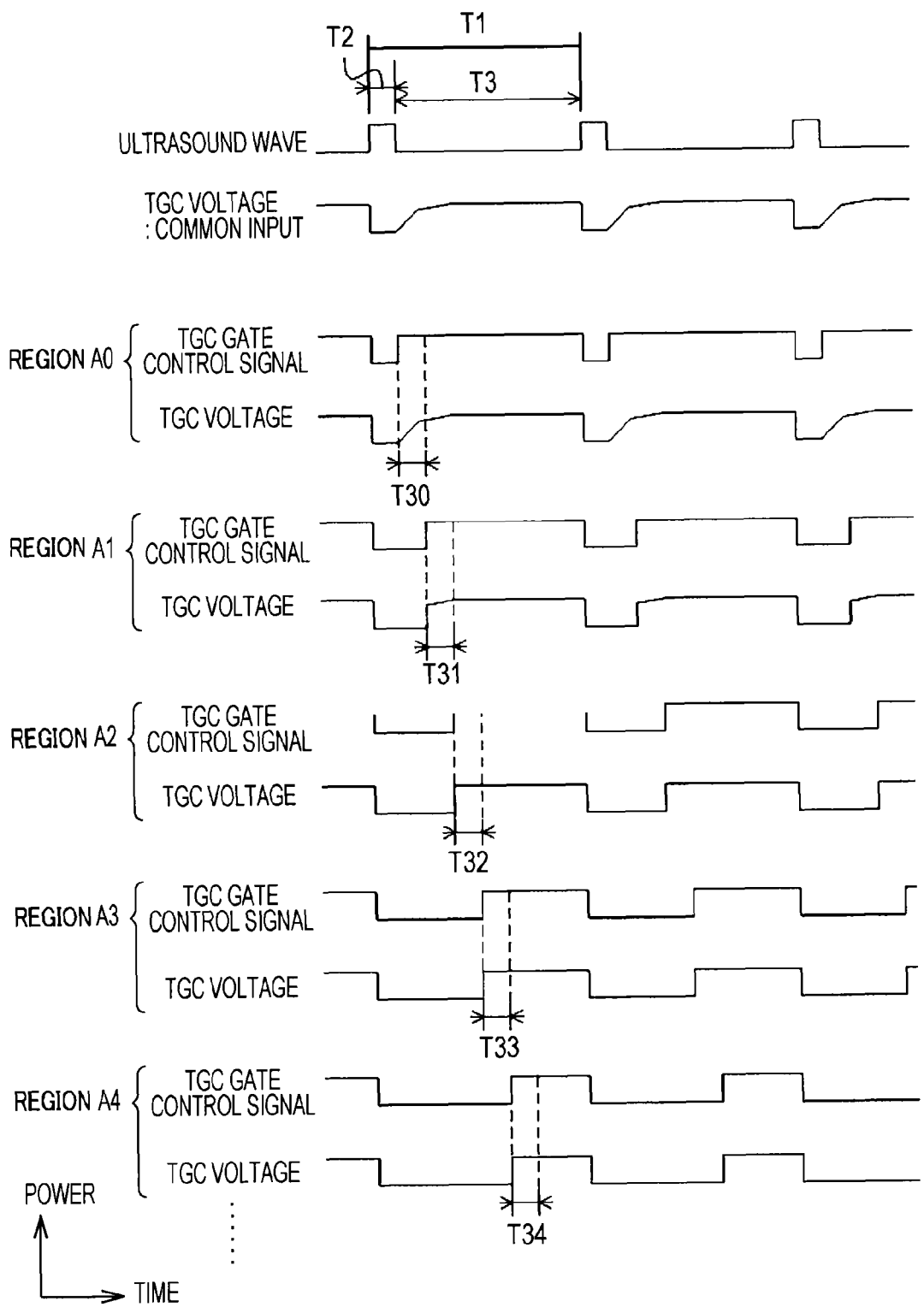
FIG. 4B is a diagram describing the control of an Aperture growth in the present embodiment.

Now, the specific control of the Aperture growth in the 2D array probe is described with reference to FIG. 4A and FIG. 4B. Referring first to FIG. 4A, FIG. 4A is a diagram in which an ultrasound transducer group 11 is viewed from the direction of transmission of ultrasound waves. The X-axis in FIG. 4A shows the X-axis direction and corresponds to the X-axis direction in FIG. 3B.

For example, a region A0 in FIG. 4A shows a region with a width W0 in both the X-axis direction and the Y-axis direction. In the case of receiving ultrasound waves reflected in the vicinity of a body surface (equivalent to period T30 in FIG. 3A) are received, this region A0 is set as a reception aperture. Assuming that the state in which the reception aperture is set to this region A0 is an initial state, regions A1, A2, . . . , and A6 are sequentially added to the initial state for each period during which ultrasound waves from a deeper depth are received (the periods T31 to T36 in FIG. 3A). By controlling in this way, the reception aperture is gradually widened depending on the timing of receiving ultrasound waves reflected at each depth. Wherein, it is sufficient as long as the reception aperture is widened depending on the depth, so the width of the X-axis direction and the Y-axis direction of the reception aperture and the shape of the reception aperture are not necessarily limited to those described above.

Next, the control of the Aperture growth in the present embodiment is described focusing on control timing with reference to FIG. 4B. The Y-axis in FIG. 4A shows the direction of a longitudinal axis that is orthogonal to the X-axis. FIG. 4B shows the control timing regarding the Aperture growth in the ultrasound diagnosis apparatus according to the present embodiment. Wherein, "TGC voltage: Common input" in FIG. 4B shows the power of the TGC voltage that the TGC voltage supply 13 supplies to the preamplifier group 12. In addition, FIG. 4B shows graphs of "TGC gate control signals" and "TGC voltage" for each region (A0 to A6) shown in FIG. 4A. The graphs of "TGC gate control signals" show the power of a control signal controlling the TGC gate circuit 17. When this control signal is input to the TGC gate circuit 17, the TGC voltage from the TGC voltage supply 13 passes through the TGC gate circuit 17 and is supplied to a corresponding preamplifier. The power of the supplied TGC voltage during this process is shown as a "TGC voltage." Wherein, in these specifications, the description of "a preamplifier corresponding to the region A0" shall indicate "a preamplifier that amplifies signals from the transducers that are included in the region A0," for example. In addition, "a TGC gate circuit corresponding to the region A0" shall indicate "a TGC gate circuit controlling the presence or absence of the supply of the TGC voltage to the amplifier amplifying signals from the transducers that are included in the region A0," for example.

First, during the period T2, ultrasound waves are transmitted from each transducer comprising the ultrasound transducer group 11 to a subject. During this period, the TGC voltage supply 13 does not supply TGC voltage to the preamplifier group 12, as shown by "TGC voltage: Common input" in FIG. 4B. Next, during the period T3, each transducer starts to receive ultrasound waves reflected from the inside of a subject. In response to the start of this period T3, the TGC voltage supply 13 starts to supply TGC voltage to the preamplifier group 12.

During the period T30, ultrasound waves reflected in the vicinity of a body surface are received by each transducer. Therefore, during the period T30, the TGC gate controller 183 starts to transmit TGC gate control signals to the TGC gate circuit 17 corresponding to the region A0, while the TGC gate control signals are not transmitted to the TGC gate circuit 17 corresponding to other regions. Accordingly, in response to the start of the period T30, the supply of the TGC voltage is started to only the preamplifier corresponding to the region A0. Thus, during the period T30, only signals from the transducers included in the region A0 are amplified by each preamplifier and input to the delay circuit group 14, while signals from the transducers included in other region are disconnected by each preamplifier. Accordingly, a reception aperture shown as the region A0 is formed.

Next, during the period T31, the ultrasound waves reflected at the depth 1 are received in each transducer. Therefore, in response to the start of the period T31, the TGC gate controller 183 starts to transmit the TGC gate control signals to the TGC gate circuit 17 corresponding to the region A1 in addition to the region A0. Accordingly, in response to the start of the period T31, the supply of the TGC voltage to the preamplifier corresponding to the region A1 is started. Thus, during the period T31, only signals from the transducers that are included in the regions A0 and A1 are amplified by each preamplifier and input to the delay circuit group 14, while signals from the transducers that are included in other regions are disconnected by each preamplifier. Accordingly, a reception aperture shown by the regions A0 and A1 is formed.

Similarly, in response to the start of each of the periods T32, T33, . . . , and T36, transmission of the TGC gate control signals to the TGC gate circuit 17 corresponding to the region A2, A3, . . . , and A6 is sequentially started. Accordingly, a reception aperture is gradually widened depending on the timing (the period T30, T31, . . . , and T36) of receiving ultrasound waves from each depth.

Figure 5:
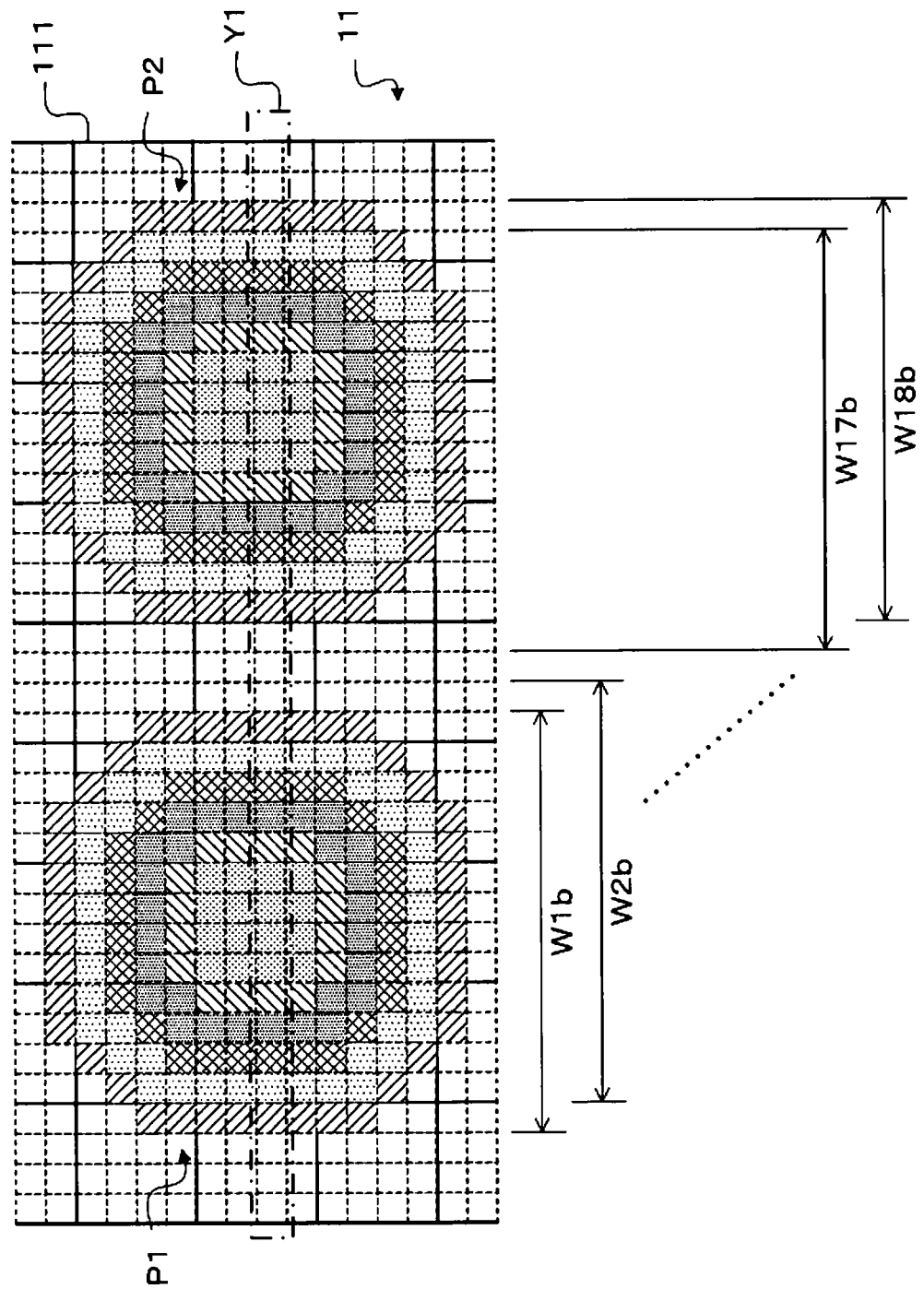
FIG. 5 is a diagram describing the control of the motion of an aperture in the present embodiment.

Wherein, although the abovementioned description was made focusing on the Aperture growth, other aperture control can be similarly performed in the transducer units. For example, as shown in FIG. 5, when an aperture is moved from a position P1 to P2, it is preferably operated such that the supply of TGC voltage to a preamplifier corresponding to transducers that are not included in the aperture is disconnected by the TGC gate circuit 17 depending on the position of the aperture in conjunction with the movement and size of the aperture. A specific operation is described focusing on transducers arranged in the X-axis direction included in the range shown by Y1. First, in the initial state, the TGC gate circuit 17 is controlled so that the TGC voltage is supplied to a preamplifier corresponding to transducers included in the region with a width W1$b$. Accordingly, an aperture is formed in the position P1. Subsequently, in response to the movement of the aperture, the TGC gate circuit 17 is controlled such that TGC voltage is supplied to a preamplifier corresponding to transducers included in the region with widths in the order of W2$b$, W3$b$, . . . W17$b$, W18$b$. Accordingly, a reception aperture is allowed to be moved from the position P1 to the position P2 in the transducer units.

In conventional ultrasound diagnosis apparatuses, this aperture control is controlled for each sub-array 111. Therefore, for example, in the case of the Aperture growth, a reception aperture was controlled in the sub-arrays 111 units in order of W0$a$, W1$a$, and W2$a$ in FIG. 3B. In contrast, the ultrasound diagnosis apparatus according to the present embodiment switches connection and disconnection for each signal line 11$a$ by switching the presence or absence of the supply of the TGC voltage for each preamplifier by the TGC gate controller 183. Accordingly, as shown by W0 to W6 in FIG. 3B, it is allowed to control an aperture for each transducer.

Second Embodiment

Figure 6:
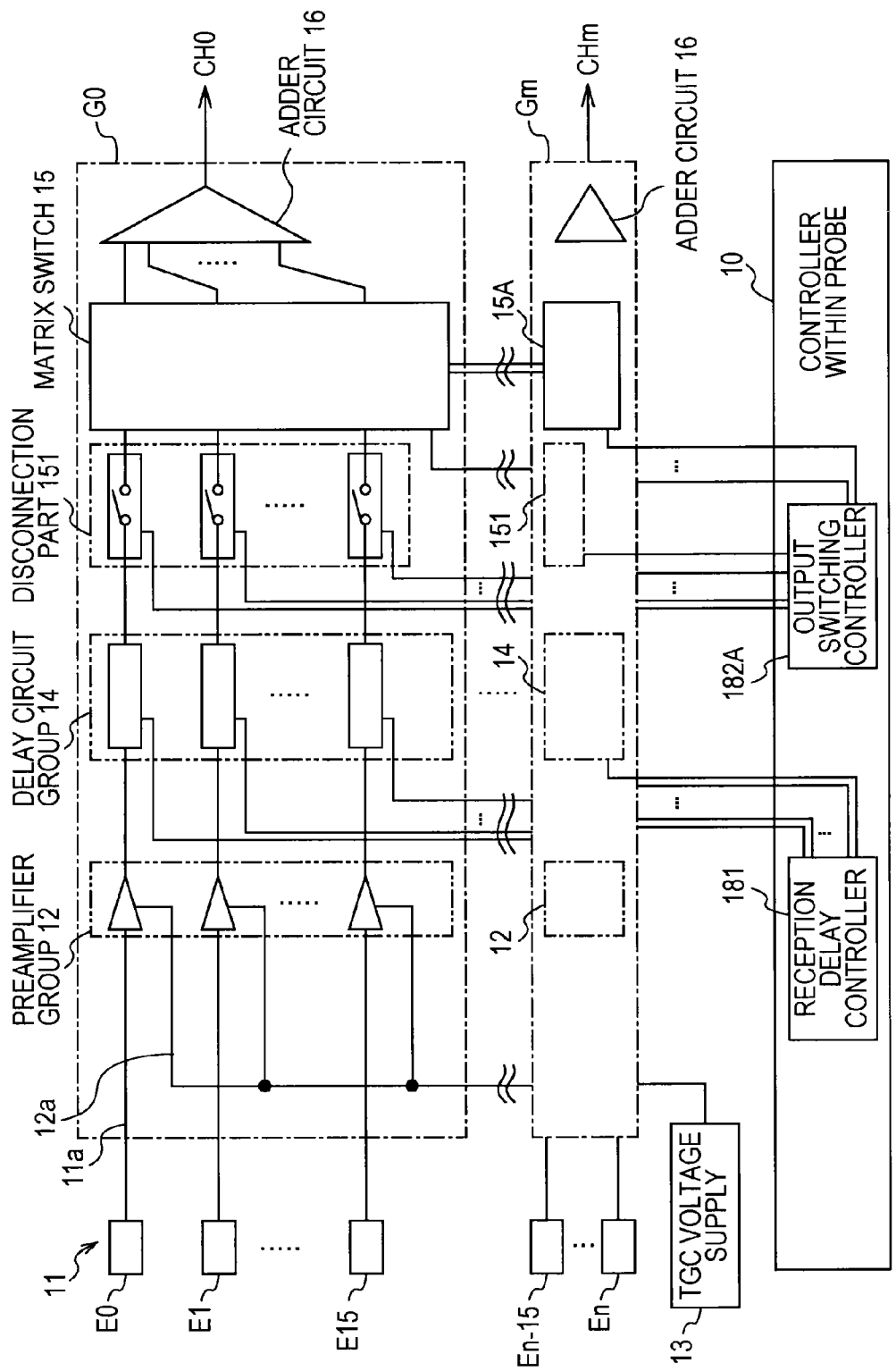
FIG. 6 is a block diagram of the reception part of the ultrasound probe according to the second embodiment.

The constitution of the ultrasound diagnosis apparatus according to the second embodiment is described with reference to FIG. 6. FIG. 6 is a block diagram of the reception part of the ultrasound probe according to the present embodiment. In the ultrasound diagnosis apparatus according to the first embodiment, connection and disconnection of the signal line 11$a$ corresponding to the preamplifier is switched by individually controlling the presence or absence of the supply of the TGC voltage to each preamplifier by the TGC gate controller 17. On the other hand, the ultrasound diagnosis apparatus according to the second embodiment provides a disconnection part 151 instead of providing the TGC gate circuit 17, which switches passage and disconnection of signals flowing on the signal line 11$a$ from each transducer. In the following, the description is made by focusing on a portion different from the first embodiment.

The disconnection part 151 is a switch configured to be able to switch passage and disconnection of signals flowing in the signal line 11$a$ for each signal line 11$a$. The switching of the disconnection part 151 is controlled by an output switching controller 182A. Wherein, although the disconnection part 151 mediates between the delay circuit group 14 and the matrix switch 15 in FIG. 7, the position is not limited thereto as long as it is provided on the signal line 11$a$ between the ultrasound transducer group 11 and the adder circuit 16.

The output switching controller 182A controls the matrix switch 15 in the same manner as the switching controller 182 according to the first embodiment. In addition, the output switching controller 182A individually controls the switching of the disconnection part 151 for each signal line 11$a$. Specifically, the output switching controller 182A controls the disconnection part 151 such that reception signals from the transducers that are included in an aperture are passed, while reception signals from the transducers not included in the aperture are disconnected. Accordingly, an aperture for each transducer is allowed to be controlled.

Wherein, when the Aperture growth is controlled, in response to the transmission timing of TGC gate control signals shown in FIG. 4A, the output switching controller 182A preferably controls the disconnection part 151 to pass reception signals flowing on corresponding signal line 11$a$. Thus, the output switching controller 182A preferably controls the disconnection part 151 such that, in response to the start of the period T30, reception signals from the transducers included in the region A0 are passed, while reception signals from the transducers included in other region are disconnected. In addition, in response to the start of each period (T31, T32, . . . , and T36), the output switching controller 182A preferably sequentially passes reception signals from the transducers included in the region (the region A1, A2, . . . , and A6) corresponding to that period. Accordingly, the reception aperture is gradually widened depending on the timing of receiving ultrasound waves from each depth (the period T30, T31, . . . , and T36). Wherein, it may be a constitution in which the same operation as the switching by the disconnection part 151 is realized by the matrix switch 15.

As described above, with the ultrasound diagnosis apparatus according to the present embodiment, an aperture for each transducer can be controlled in the same manner as the first embodiment by controlling the pass and disconnection of reception signals by the disconnection part 151 instead of controlling the TGC voltage supply using the TGC gate circuit 17 according to the first embodiment.

Third Embodiment

Figure 7:
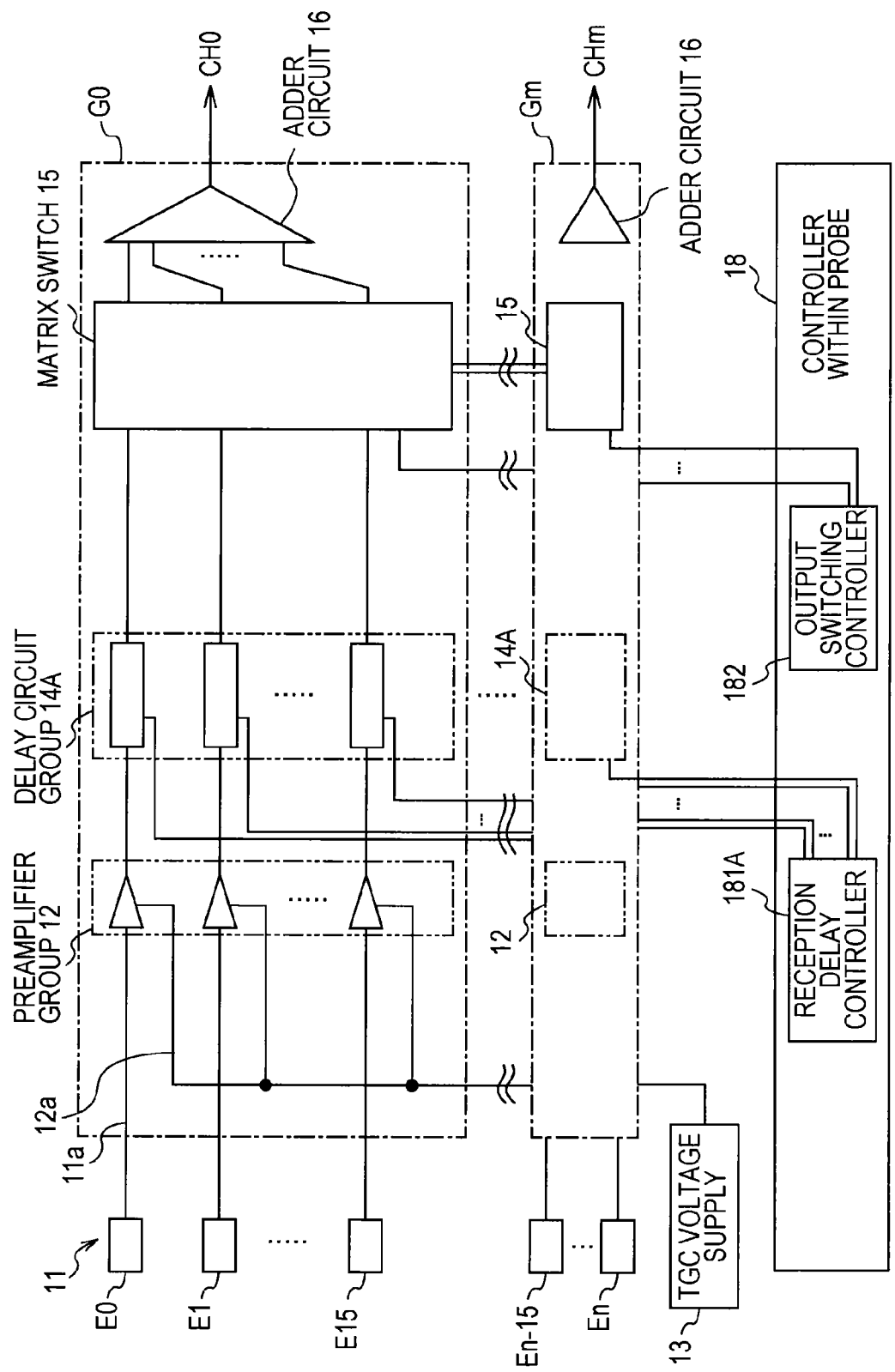
FIG. 7 is a block diagram of the reception part of the ultrasound probe according to the third embodiment.

The constitution of the ultrasound diagnosis apparatus according to the third embodiment is described with reference to FIG. 7. FIG. 7 is a block diagram of the reception part of the ultrasound probe according to the present embodiment. The ultrasound diagnosis apparatus according to the third embodiment switches passage and disconnection of signals flowing in the signal line 11$a$ from each transducer by each delay circuit comprising the delay circuit group 14 instead of providing the TGC gate circuit 17. In the following, a description is made focusing on portions different from the first embodiment.

The reception circuit group 14A according to the present embodiment is characterized in that a multiplier circuit is employed as a delay circuit. A specific example of the multiplier circuits includes a mixer. The delay circuit according to the present embodiment receives reference signals as delay data from a reception delay controller 181A. The delay circuit shifts the phase of the reception signals by which these reference signals are multiplied (mixed), with respect to the reception signals that are received from the preamplifier group 12. In other words, a delay processing is performed to the reception signals by changing these reference signals depending on the delay.

The reception delay controller 181A calculates the necessary delay based on the distance between a transducer and a focus point of the inside of a subject for each transducer comprising the ultrasound transducer group 11. This operation is the same as that of the delay controller 181 according to the first embodiment. The reception delay controller 181A generates reference signals by which the reception signals from the transducers are multiplied, based on the calculated delay. The reception delay controller 181A controls the operation of the delay circuit by outputting the generated reference signals as delay data to the delay circuit connected to the transducer corresponding to the delay. The case in which the reference signals for performing a delay processing to reception signals in this way is equivalent to "the case in which the reference signals include delay instructions."

In addition, the reception delay controller 181A stops the transmission of the reference signals to the delay circuit corresponding to the transducers not included in the aperture. In this case, the reference signals are not supplied to the delay circuit, resulting in the reception signals input to this delay circuit not being output to the matrix switch 15 located at a subsequent stage. In other words, the reception signals are disconnected by stopping the transmission of the reference signals. During this process, the delay circuit may be of a constitution in which reception signals escape to the ground. The case in which the reference signals are not output to the delay circuit is equivalent to "the case in which the reference signals include disconnection instructions." Accordingly, the passage and disconnection of the reception signals output from each transducer is allowed to be controlled individually. In other words, an aperture for each transducer can be controlled.

Wherein, when the Aperture growth is controlled, in response to the transmission timing of TGC gate control signals shown in FIG. 4A, the reception delay controller 181A preferably controls the delay circuit to pass reception signals flowing in the corresponding signal line 11*a*. In other words, in response to the start of the period T30, the reception delay controller 181A transmits reference signals to the delay circuit corresponding to the transducers included in the region A0. Accordingly, the delay circuit passes the reception signals from these transducers. In addition, during the process, the reception delay controller 181A does not transmit reference signals to the delay circuit corresponding to the transducers not included in the region A0. Accordingly, the delay circuit disconnects the reception signals from these transducers. In addition, in response to the start of each period (T31, T32, . . . , and T36), the reception delay controller 181A preferably sequentially transmits reference signals to the delay circuit included in the region (the region A1, A2, . . . , and A6) corresponding to that period. Accordingly, the reception aperture is allowed to be gradually widened by sequentially passing the signals in the corresponding region depending on the timing (the period T30, T31, . . . , T36) of receiving ultrasound waves from each depth.

As described above, with the ultrasound diagnosis apparatus according to the present embodiment, an aperture for each transducer can be controlled in the same manner as the first embodiment by controlling the transmission of delay data to each delay circuit instead of controlling the TGC voltage supply using the TGC gate circuit 17 according to the first embodiment.

Although some embodiments of the present invention have been described above, these embodiments are presented as examples and are not intended to limit the scope of the invention. These novel embodiments can be implemented in other various forms, with various abbreviations and exchanges, and changes can be made within a scope not departing from the essence of the invention. These embodiments and their modifications are included in the scope and essence of the invention and are included in the invention described in the claims, along with the equal scope thereof.

EXPLANATION OF THE SYMBOLS

1 Ultrasound probe
10 Transmission circuit
11 Ultrasound transducer group
12 Preamplifier group
13 TGC voltage supply
14,14A Delay circuit group
15 Matrix switch
151 Disconnection part
16 Adder circuit
17 TGC gate circuit
18 Controller within probe
181, 181A Reception delay controller
182, 182A Output switching controller
183 TGC gate controller
2 Main body reception part
20 Reception main delay circuit
21 Signal processor
22 Image processor
23 Display part

What is claimed is:

1. An ultrasound probe, comprising:
a plurality of ultrasound transducers configured to transmit ultrasound waves at a predetermined cycle and receive ultrasound echoes from inside of a subject;
a plurality of delay circuits configured to receive reception signals from each of the ultrasound transducers and apply a delay processing to each of the reception signals;
an adder circuit configured to add and output the reception signals to which the delay processing is performed for each predetermined group of a plurality of groups, wherein the ultrasound probe is configured to control a reception aperture of the ultrasound waves; and
a gate circuit configured to switch connection and disconnection of signal paths for each signal path arranged between an ultrasound transducer of the plurality of ultrasound transducers and the adder circuit, and connect only the signal path from the ultrasound transducer corresponding to an initial reception aperture that is previously set after transmitting the ultrasound waves within the cycle of the ultrasound waves, and sequentially connect corresponding signal paths from ultrasound transducers outside the initial reception aperture according to a lapse in time of a reception period.

2. The ultrasound probe according to claim 1, wherein the gate circuit further comprises preamplifiers that mediate in the signal paths between the ultrasound transducers and the delay circuits and amplify the reception signals, the ultrasound probe further comprising:

a gain control voltage supply unit configured to supply gain control voltages for controlling gains of the preamplifiers; and a gain control gate circuit configured to control supply and disconnection of the gain control voltages to the preamplifiers, wherein the gain control gate circuit is configured to control the reception aperture by supplying the gain control voltages to the gain control gate circuit to individually connect the signal paths from the preamplifiers to the delay circuits.

3. The ultrasound probe according to claim 1, wherein the gate circuit further comprises a switch that mediates in the signal paths between the delay circuits and the adder circuit, and the switch is configured to control the reception aperture by switching connection and disconnection of the signal paths between the delay circuits and the adder circuit for each signal path.

4. The ultrasound probe according to claim 1, wherein each delay circuit is a multiplier circuit configured to receive reference signals including either delay instructions or disconnection instructions and multiply the reference signals by the reception signals, the multiplier circuit is configured to perform the delay processing to the reception signals and output reception signals to which the delay processing has been performed when the reference signals include delay instructions, the multiplier circuit is configured to disconnect the output of the reception signal when the reference signals include disconnection instructions, and the delay circuit is configured to switch reference signals to the delay circuits to control the reception aperture.

5. An ultrasound diagnosis apparatus, comprising:

a plurality of ultrasound transducers configured to transmit ultrasound waves at a predetermined cycle and receive ultrasound echoes from inside of a subject;

a plurality of delay circuits configured to receive reception signals from each of the ultrasound transducers and apply a delay processing to each of the reception signals;

an adder circuit configured to add and output the reception signals to which the delay processing is performed for each predetermined group;

an ultrasound probe configured to control a reception aperture of the ultrasound waves, wherein the ultrasound diagnosis apparatus is configured to receive the reception signals output from the ultrasound probe and perform a phasing and addition operation on the reception signals to generate an ultrasound image, and the ultrasound probe further comprises a gate circuit configured to switch connection and disconnection of the signal path for each signal path arranged between an ultrasound transducer of the plurality of ultrasound transducers and the adder circuit, and connect only a signal path from an ultrasound transducer corresponding to an initial reception aperture that is previously set after transmitting the ultrasound waves within the cycle of the ultrasound waves, and sequentially connect corresponding signal paths from ultrasound transducers outside the initial reception aperture according to a lapse in time of a reception period.

6. An ultrasound probe, comprising:

a plurality of ultrasound transducers configured to transmit ultrasound waves and receive ultrasound echoes from inside of a subject;

a plurality of delay circuits configured to receive reception signals from each of the ultrasound transducers and apply a delay processing to each of the reception signals; and an adder circuit configured to add and output the reception signals to which the delay processing is performed for each predetermined group; and a gate circuit configured to switch the connection and disconnection of a signal path for each signal path arranged between an ultrasound transducer of the plurality of ultrasound transducers and the adder circuit.

* * * * *